US012377253B2

(12) United States Patent
Castellucci et al.

(10) Patent No.: US 12,377,253 B2
(45) Date of Patent: Aug. 5, 2025

(54) APPLICATOR FOR IMPLANT INSERTION

(71) Applicant: CHEMO RESEARCH, S.L., Madrid (ES)

(72) Inventors: Alessandro Castellucci, Guadalajara (ES); Roberto Pérez, Guadalajara (ES)

(73) Assignee: CHEMO RESEARCH, S.L., Madrid (ES)

( * ) Notice: Subject to any disclaimer, the term of this patent is extended or adjusted under 35 U.S.C. 154(b) by 0 days.

(21) Appl. No.: 18/488,828

(22) Filed: Oct. 17, 2023

(65) Prior Publication Data

US 2025/0121170 A1 Apr. 17, 2025

(51) Int. Cl.
*A61M 37/00* (2006.01)
(52) U.S. Cl.
CPC ..... *A61M 37/0069* (2013.01); *A61M 2210/04* (2013.01)
(58) Field of Classification Search
CPC ...... A61M 2005/2013; A61M 37/0069; A61M 31/007; A61M 5/46; A61M 2205/13; A61M 39/28; A61M 39/281; A61M 39/284; A61B 2090/036
See application file for complete search history.

(56) References Cited

U.S. PATENT DOCUMENTS

| | | | | |
|---|---|---|---|---|
| 4,994,028 A | * | 2/1991 | Leonard | A61M 37/0069 604/59 |
| 2010/0298807 A1 | * | 11/2010 | Jansen | A61M 37/0069 604/60 |
| 2023/0173242 A1 | * | 6/2023 | Clark | A61M 37/0069 604/60 |
| 2024/0074829 A1 | * | 3/2024 | Rousche | A61M 5/162 |

* cited by examiner

*Primary Examiner* — Nathan R Price
*Assistant Examiner* — Anna E Goldberg-Richmeier
(74) *Attorney, Agent, or Firm* — Seed IP Law Group LLP (57) ABSTRACT

Embodiments of the invention relate to an applicator for inserting an implant under the skin of a patient. The applicator comprises a housing containing a cannula that is fixed to a cannula holder and is slidably received within said housing. The cannula comprises an aperture at its distal end and a lateral opening. The implant is accommodated within the cannula and/or the cannula holder. A securing mechanism retains the implant inside the cannula. This mechanism comprises an arm configurable between a first position, which prevents the implant from exiting through the cannula's aperture, and a second position that enables the implant's placement under the skin through the aperture. Said lateral opening is situated between the aperture and the distal end of the implant. In the first arm position, the arm partially enters the lateral opening, thereby obstructing the implant from exiting through the aperture.

25 Claims, 7 Drawing Sheets

APPLICATOR FOR IMPLANT INSERTION

TECHNICAL FIELD

The present invention belongs to the field of biomedical engineering, particularly to the field of implant insertion. More particularly, the present invention relates to a device for intradermal implant insertion comprising a cannula, a cannula holder, an implant accommodated inside the cannula and/or the cannula holder, and a mechanism which secures the implant inside the cannula and/or the cannula holder.

BACKGROUND

Intradermal implants, particularly those containing hormones, have been a significant advancement in the field of medicine and healthcare. They are typically small, thin rods that are inserted under the skin of a patient, usually in the upper arm. These implants release drugs or hormones into the body over a set period, often several years, providing a long-term, reversible drug or hormone delivery system. One of the main use cases of such a system is as a method of contraception.

The use of intradermal implants as contraceptives has several advantages. First, they offer a long-term solution for contraception, with some implants effective for up to three to five years. This eliminates the need for daily or monthly contraceptive methods, making it a convenient option for many individuals. Second, they are highly effective, with less than 1 in 100 women becoming pregnant each year while using the implant. Third, they are reversible, meaning fertility can return quickly after the implant is removed. Finally, they can be used during breastfeeding and do not interfere with sexual intercourse.

There are several applicators known for being capable of inserting a rod-like implant under the skin. These applicators are designed to be user-friendly and secure, allowing to use them with one hand and comprising features that aim to reduce the risk of premature implant expulsion and enhance the precision of implant placement. An example of such applicator comprises a housing, a cannula for accommodating the implant, a cannula holder, a rod mounted on or in the housing and at least partially inside the cannula and/or the cannula holder, an actuator for sliding the cannula and the rod relative to each other to expel the implant from the cannula, and a handle for grasping and maneuvering the applicator and the cannula during insertion of an implant. This design allows for a more controlled and secure insertion process, potentially reducing the risk of complications and increasing the effectiveness of the implant.

However, despite the advantages of this applicator, it does not prevent the implant from sliding out before insertion, which can lead to complications during the insertion process. To address this issue, there exist applicators with a mechanism that secures the implant inside the cannula and/or the cannula holder after the cover has been removed from the cannula. This mechanism disengages the implant during or after the insertion of the cannula, and it comprises a lever or protrusion extending along at least part of the cannula, which is rotatable and/or slidable and/or flexible between a first position wherein the implant is secured inside the cannula and/or the cannula holder and a second position wherein the implant is disengaged. The cannula and/or the cannula holder comprise an opening which allows access to the implant, and the lever comprises a protrusion in register with this opening. The lever is biased towards the cannula and/or the cannula holder such that the protrusion urges the implant against the inner wall of the cannula or the cannula holder.

While this mechanism addresses the issue of premature implant expulsion, it introduces a new set of challenges. The pressing of the protrusion against the implant or the cannula can increase the risk of breaking or damaging the implant, leading to further complications.

Other applicators include protrusions in the lumen of the cannula or localized reductions in its diameter, in order to secure the implant inside said cannula. These protrusions, while preventing the implant to unwantedly slide out of the cannula, also exert a continuous pressing force over the implant, forcing it against the walls or against the protrusions. This poses a risk of damaging the implant during the whole shelf life of the applicator. Furthermore, said protrusions also exert a shearing force on the surface of the implant during application, when the implant is sliding out of the cannula, causing it to rub and/or to scratch against said protrusions. Again, this way of securing the implant by applying a constant pressure over it increase the likelihood of damaging or fracturing the implant, which may result in additional complications.

Therefore, there is a need for an implant insertion device that is precise, easy to use, can be operated with one hand and secures the implant before insertion, but at the same time avoids or reduces the risk of breaking, damaging, or modifying the implant in any way. Such a device would provide a safer and more reliable method for the insertion of intradermal implants, potentially increasing their use and effectiveness as a contraceptive method.

BRIEF SUMMARY

Embodiments of the invention relate to an applicator for inserting an implant under the skin of a patient. The applicator comprises a) a housing; b) a cannula, fixed to a cannula holder, which is slidably received inside the housing, wherein the cannula comprises an aperture on its distal end and a lateral opening; c) an implant accommodated inside the cannula and/or the cannula holder, and d) a mechanism that secures the implant inside the cannula and/or the cannula holder, wherein the mechanism comprises an arm which is rotatable and/or slidable and/or flexible between a first position, wherein the arm prevents the implant from exiting the cannula through the aperture, and a second position, wherein the arm allows the implant to exit the cannula through the aperture, thereby allowing the placement of the implant under the skin of the patient.

In certain embodiments the lateral opening of the cannula is positioned between the aperture of the cannula and the distal end of the implant, and in that in the first position of the lever, said lever is configured to be at least partially introduced within the lateral opening of the cannula, preventing thus the implant from exiting the cannula through the aperture.

In a preferred embodiment the applicator is configured such that when the cannula is inserted under the skin of a patient, skin on top of the cannula sets the arm into its second position, outside of the lateral opening of the cannula, such that it allows the implant to slidably exit the cannula through the aperture.

In another preferred embodiment the applicator further comprises elastic means that interact with the mechanism to push the arm to the first position and into the lateral opening of the cannula, preferably the elastic means is a bended surface or a spring, more preferably it is metallic.

In another preferred embodiment the applicator further comprises a stopper surface that surrounds the cannula and/or the cannula holder, and defines the limit of insertion of the cannula under the skin of a patient.

In another preferred embodiment the applicator further comprises a rod mounted on or in the housing and at least partially inside the cannula and/or the cannula holder; and an actuator for sliding the cannula and the rod relative to each other to expel the implant from the cannula.

In a more preferred embodiment, the housing further comprises a handle for grasping and maneuvering the applicator and the cannula during insertion of an implant, preferably wherein the actuator is located on the handle.

In another more preferred embodiment the cannula holder is slidable over the rod, and the actuator and the holder are interconnected, preferably by a flexible element, more preferably wherein the flexible element is at least partially retained by guides.

In a preferred embodiment of any one of the more preferred embodiments above-mentioned, the handle and/or the actuator are provided with surface parts that have a relatively high coefficient of friction, wherein preferably they comprise at least one or more protrusions to improve the grip over the surface.

In another more preferred embodiment the housing further comprises a protrusion that blocks the actuator in an initial position before actuating the applicator and prevents it from sliding towards the proximal end of the housing, preferably until it is pushed to evade said protrusion, more preferably until it is pushed downwards to evade said protrusion.

In another preferred embodiment of any of the previous embodiments, the applicator further comprises a back cover attached to the rod, preferably wherein the back cover is not removable from the proximal end of the housing.

In a more preferred embodiment the back cover further comprises a flange that engages with a protrusion in the cannula holder, which blocks the actuator in a final position after actuating the applicator.

In another preferred embodiment of any of the previous embodiments, the implant comprises an active substance for insertion under the skin of a patient, preferably the implant contains a progestogenic hormone, more preferably contains etonogestrel.

In another preferred embodiment, the applicator is configured to allow the insertion of an implant inside the cannula and/or cannula holder through the proximal end of the housing before assembling the back cover.

In another preferred embodiment the applicator further comprises a protective cover for the cannula and/or the cannula holder. In a more preferred embodiment, the arm is configured to remain in the same position independently of the removal or the application of the protective cover the cannula and/or the cannula holder.

BRIEF DESCRIPTION OF THE DRAWINGS

To enable a better understanding of the present disclosure, and to show how the present disclosure may be carried out, reference will now be made, by way of example only, to the accompanying schematic drawings, wherein.

DETAILED DESCRIPTION

It must be noted that, as used herein, the singular forms "a", "an", and "the", include plural references unless the context clearly indicates otherwise. Further, unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the present invention.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having". Any of the aforementioned terms (comprising, containing, including, having), whenever used herein in the context of an aspect or embodiment of the present invention may be substituted with the term "consisting of", though less preferred.

When used herein "consisting of" excludes any element, step, or ingredient not specified in the claim element. When used herein, "consisting essentially of" does not exclude materials or steps that do not materially affect the basic and novel characteristics of the claim.

The term "applicator", in the context of the invention, refers to a device that comprises at least a housing, a cannula, and may comprise an implant accommodated inside the cannula. Said applicator allows the insertion of an implant under the skin of a patient by introducing first the cannula comprising the implant under the skin, and then allowing the implant to exit the cannula.

The term "implant", in the context of the invention, refers to a small piece that is inserted under the skin of a patient, preferably intradermally. The implant may adopt different shapes, such as a rod, and different materials, such as plastic, and may be flexible or rigid. The implant may also comprise an active substance, such as, for instance, a hormone or a contraceptive substance.

The term "cannula", in the context of the invention, refers to a thin tube that is inserted under the skin of a patient. The cannula may comprise a pointy and angled aperture in the distal end to facilitate the insertion, and it may comprise a medical grade material such as surgical stainless steel. The cannula may have an adequate diameter to comprise an implant inside the lumen of the tube.

The term "lateral opening", in the context of the invention, refers to an orifice comprised between the proximal and distal ends of the cannula, i.e., an orifice comprised along the side of the cannula's shaft, separate from the entrance (proximal end) and exit (distal end) apertures.

The term "aperture", in the context of the invention, refers to an opening or passageway situated at the proximal or distal ends of the hollow tube, through which the implant may enter or exit the cannula.

The term "arm," in the context of the invention, refers to a mechanical component integrated in the applicator, configured to enter the cannula at least partially through a lateral opening in said cannula, preventing the implant from exiting through the cannula's distal end. Upon insertion of the cannula under the skin, the arm may be lifted upwards, thereby allowing the implant to exit through the distal end of the needle.

The term "actuator", in the context of the invention, refers to any mechanical or electronic component designed to initiate or control the movement of the applicator, facilitating the placement of an intradermal implant into the patient. The actuator may come in various forms, such as, but not limited to, a button, lever, switch, or knob, and may be pushed, pulled, or otherwise manipulated to trigger or guide the cannula and release the implant into its intended position under the skin of a patient.

The term "patient", in the context of the invention, refers to the recipient of the intradermal implant, and may be either a human being or an animal.

Intradermal implants, such as those used for hormone release, have revolutionized healthcare by offering a convenient, highly effective, and reversible form of long-term treatment. Existing applicators aim to make the implant insertion process user-friendly, secure, and precise, with features that minimize the risk of premature implant expulsion. While these designs advance the state of the art, they fall short in key areas: the risk of the implant sliding out prematurely still exists, or pressing mechanisms used to hold the implant in place can inadvertently damage it. This poses challenges and risks that can potentially lead to complications during and after the implant insertion. As a result, there is a clear need for a new implant insertion device that is not only easy to operate and secure but also minimizes the risk of damaging the implant. The present invention provides a solution to these challenges, offering a safer and more reliable method for intradermal implant insertion.

Here we disclose an applicator for inserting an implant, as illustrated in FIGS. 1 to 9, that allows securing the implant inside the cannula without damaging said implant, by comprising a lateral opening whereby an arm may enter, at least partially, to block the passageway and prevent the implant from exiting. Therefore, the arm does not need to press the implant against the walls of the cannula to secure it, avoiding thus any associated risk of damage. Said arm may be lifted upon insertion of the cannula under the skin of a patient, due to the skin being positioned between the arm and the lateral opening, allowing thus the implant to exit the cannula and be placed intradermally.

Therefore, a first aspect of the invention discloses an applicator (1), as illustrated in FIGS. 1 to 9, for inserting an implant (50) under the skin (52) of a patient. Said applicator (1) comprises i) a housing (10), ii) a cannula (30), fixed to a cannula holder (22), which is slidably received inside the housing (10), wherein the cannula (30) comprises an aperture (32) on its distal end and a lateral opening (34), iii) an implant (50) accommodated inside the cannula (30) and/or the cannula holder (22), preferably wherein the implant is rod-like and iv) a mechanism (40) that secures the implant (50) inside the cannula (30) and/or the cannula holder (22), wherein the mechanism (40) comprises an arm (42) which is rotatable and/or slidable and/or flexible between a first position, wherein the arm (42) prevents the implant (50) from exiting the cannula (30) through the aperture (32), and a second position, wherein the arm (42) allows the implant (50) to exit the cannula (30) through the aperture (32), thereby allowing the placement of the implant (50) under the skin (52) of the patient. In some embodiments the lateral opening (34) of the cannula (30) is positioned between the aperture (32) of the cannula (30) and the distal end (54) of the implant (50), and in that in the first position of the arm (42), said arm (42) is configured to be at least partially introduced within the lateral opening (34) of the cannula (30), preventing thus the implant (50) from exiting the cannula (30) through the aperture (32).

Figure 1A:
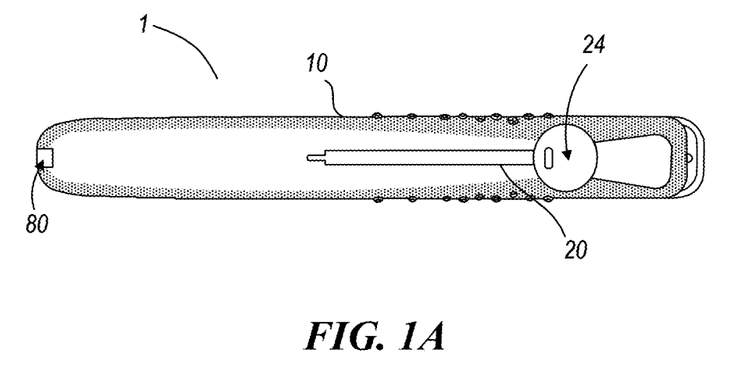
FIG. 1A shows a top view of an applicator according to one or more preferred embodiments of the invention.
Figure 1B:
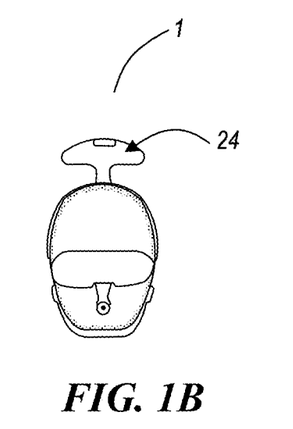
FIG. 1B shows a front view of an applicator according to one or more preferred embodiments of the invention.
Figure 2:
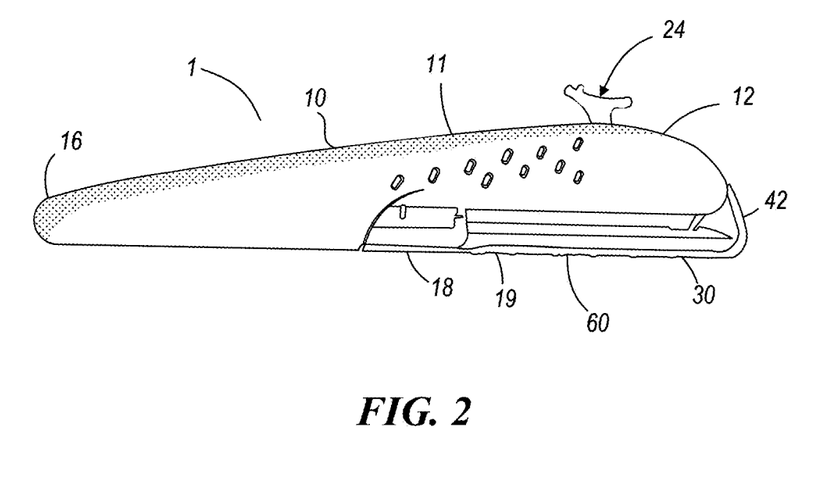
FIG. 2 shows a lateral view of an applicator comprising a protective cover according to one or more preferred embodiments of the invention.

FIGS. 1A, 1B and 2 show a top view, frontal view and lateral view of the applicator (1) according to one or more embodiments of the invention. The housing (10) shown in said figures presents an elongated shape with rounded edges, however it is noted that the shape and size of the housing (10) may vary across different embodiments of the invention, therefore it may be longer or shorter, thicker or thinner, or adopt different colours, such as white, blue or green, preferably white, or different shapes, as long as it allows to insert an implant (50) under the skin (52) of a patient. It is noted that the applicator (1) illustrated in FIGS. 1A, 1B and 2 allows to insert an implant (50) under the skin (52) of a patient with one hand and in an easy way, however, the applicator (1) may also be used with both hands, or other embodiments of the invention may require both hands. The housing (10) may also comprise different features for a more ergonomic handling that may not be represented in the figures, such as protrusions or cavities that provide a better grip for the hand, that present an ergonomic shape, or that are adapted to the shape of the hand or the fingers. These adaptations aim to enhance maneuverability and enable a firmer hold during the process of inserting the implant (50) under the skin (52) of the patient. The housing (10) may be fabricated from a variety of materials that are suitable for medical applications, wherein these materials may include, but are not limited to, hypoallergenic materials, plastics, medical-grade plastics, metals, stainless steel, aluminium, titanium, or combinations thereof. Preferably, the housing (10) is made from a hypoallergenic material to minimize the risk of allergic reactions. The choice of material may also affect the weight, durability, and overall feel of the housing (10), and may be chosen based on specific medical and operational needs. Furthermore, the housing (10) may be composed of materials that facilitate sterilization processes, such as autoclaving, or materials that are suitable for single-use, disposable applications.

Figure 3:
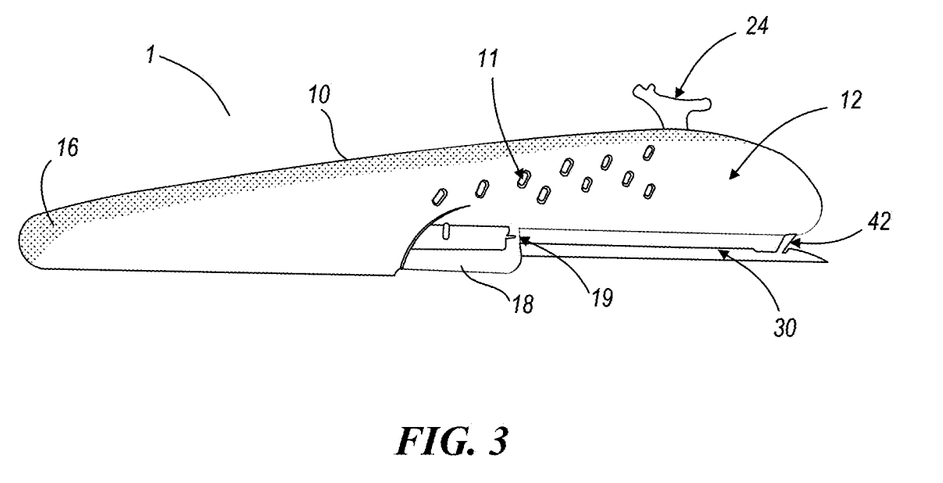
FIG. 3 shows a lateral view of an applicator according to one or more preferred embodiments of the invention.
Figure 6:
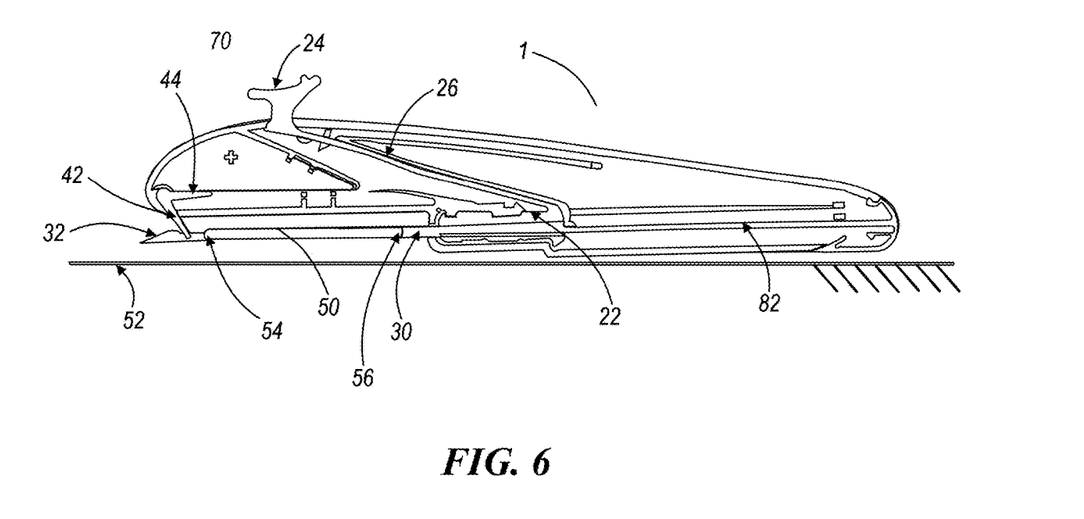
FIG. 6 shows a cross sectional side view of an applicator according to one or more preferred embodiments of the invention.
Figure 7:
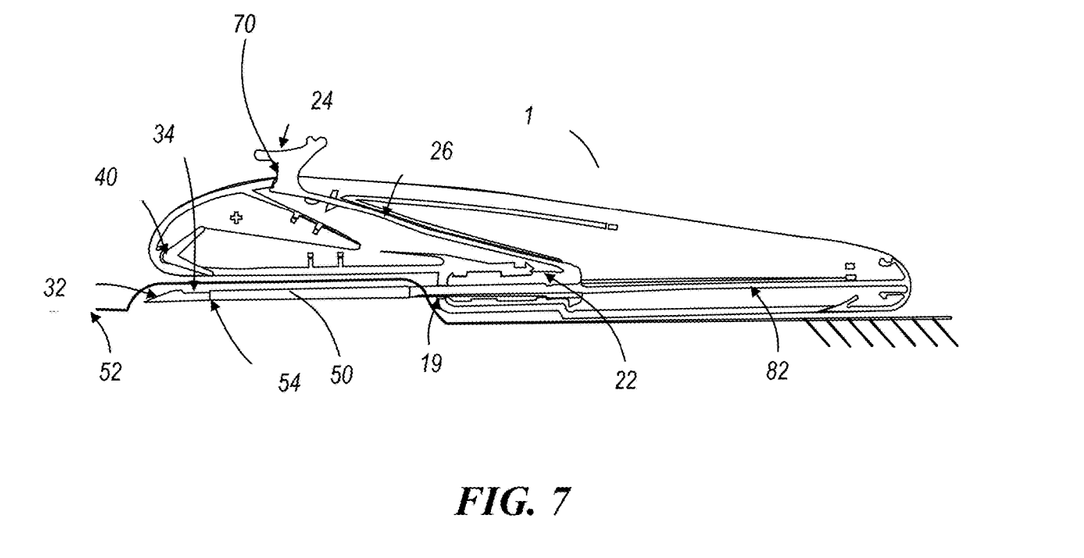
FIG. 7 shows a cross sectional side view of an applicator with the cannula inserted below the skin of a patient, according to one or more preferred embodiments of the invention.

FIG. 3 shows a lateral view of the applicator (1) for inserting an implant (50) according to one or more embodiments of the invention. The cannula (30) is displayed as a hollow tube, see also FIG. 4 with a exploded view of the components of the applicator (1), fixed to a cannula holder (22), however, it should be understood that the shape, dimensions, and material of the cannula (30) may vary within the scope of the invention. For example, the cannula (30) may be longer or shorter, or thicker or thinner than what is illustrated in the figures, depending on the specific medical requirements or the nature of the implant (50) to be inserted. Similarly, the cannula (30) may be attached to a cannula holder (22) in some embodiments, as is depicted in FIG. 5 to 7, or both may be comprised in a single or different element in alternative embodiments of the invention. Materials suitable for the construction of the cannula (30) include, but are not limited to, medical-grade stainless steel, titanium, nickel-titanium alloys, medical-grade plastics, or other biocompatible materials capable of piercing the skin (52). These materials may be chosen based on their mechanical properties, such as tensile strength, as well as their compatibility with sterilization techniques, such as autoclaving or gamma irradiation. It is further noted that the aperture (32) at the distal end of the cannula (30) may be designed to facilitate skin penetration, as is better shown in FIGS. 5 to 7, wherein the distal end of the cannula (30) ends in an angled and pointy end, following a regular needle tip section. However, the shape and/or orientation of the aperture (32) may vary across different embodiments, for instance it may be angled, beveled, or rounded, among other options, to optimize ease of penetration through the skin (52) of the patient.

The cannula (30) also features a lateral opening (34), as it is shown in FIGS. 4 to 8, positioned between the aperture (32) of the cannula and the distal end (54) of the implant (50). The lateral opening (34), therefore, may be situated in such a way that it is not aligned with the implant (50) housed inside the cannula (30). This ensures that the arm (42), when engaged in the first position, does not exert pressure on the implant (50). This lateral opening (34) may vary in size, shape, and location, as long as it allows the arm (42) to enter partially or completely into the lateral opening (34) in its first position. This way, the arm can obstruct the passageway of the implant (50) towards the aperture (32) at the distal end of the cannula (30), thereby securing said implant (50) inside the cannula (30), without the need of pressing the implant (50) against the walls of the cannula (30) to prevent the implant (50) from moving. Therefore, the lateral opening (34) may be circular, elliptical, or any other shape that permits the arm (42) to be partially or completely introduced into it. The dimensions of the lateral opening (34) are such that it allows sufficient space for the arm (42) to enter and obstruct the internal passageway leading to the aperture (32) at the distal end of the cannula (30). Alternatively, the lateral opening (34) may extend over the implant (50) as long as the functionality of the mechanism (40) to secure the implant (50) is not compromised, such as part of the lateral opening (34) being positioned over, or aligned with, part of the implant (50), given that the lateral opening (34) is big or long enough to allow the arm (42) to enter the lateral opening (34) without pressing against the implant (50). In an alternative but equivalent definition, it may be understood that the implant (50) is positioned between the lateral opening (34) and the proximal end of the cannula (30) or the cannula holder (22), or between the first position of the arm (42) and the proximal end of the cannula (30).

As it can be seen in FIGS. 4 to 8, the implant (50) may adopt a cylindrical or rod-like shape, however, the implant may be bigger, smaller, longer or shorter, or thicker or thinner, than what is illustrated in the figures, and present different aspect ratios with respect to the applicator (1). The images, thus, should be understood as merely illustrative and non-limiting. Alternatively, the implant (50) may adopt other shapes in different embodiments, such as a planar shape, a disc shape or prism-like, among others, as long as it can be delivered under the skin (52) of a patient. The cannula (30), then, may adopt different shapes that conform to the shape and/or size of the implant (50), therefore allowing the applicator (1) of the invention to deliver the implant (50).

Advantageously, the positioning of the lateral opening (34) between the aperture (32) of the cannula (30) and the distal end (54) of the implant (50), allows to secure the implant (50) inside the cannula (30) without the risk of damaging the implant (50) by directly pressing it against the walls of the cannula (30). This design therefore offers enhanced safety and reliability in the implantation procedure, ensuring a precise and controlled placement of the implant (50) under the skin (52) of the patient.

In a preferred embodiment of the applicator (1) of the invention, said applicator (1) is configured such that when the cannula (30) is inserted under the skin (52) of a patient, skin (52) on top of the cannula (30) sets the arm (42) into its second position, outside of the lateral opening (34) of the cannula (30), such that it allows the implant (50) to slidably exit the cannula (30) through the aperture (32).

FIG. 6 shows the mechanism (40) that secures the implant (50) inside the cannula (30) and/or the cannula holder (22), wherein the arm (42) comprised in said mechanism (40) is in its first position, partially inside the lateral opening (34) of the cannula (30) and effectively blocking the passageway of the implant (50) towards the exit (32), at the distal end of the cannula (30). FIG. 7 shows the arm (42) in its second position, wherein the skin (52) of the patient has been situated between the arm (42) and the cannula (30), therefore moving said arm (42) outside the lateral opening (34) of the cannula (30), therefore not blocking anymore the passageway to the implant (50) towards the exit, or aperture (32), of the cannula (30). It is noted that the mechanism (40) that secures the implant (50) inside the cannula (30) and/or the cannula holder (22) may comprise different materials, such as, but are not limited to, plastics, medical-grade plastics, stainless steel, aluminium, titanium, or combinations thereof. It may also comprise different shapes or sizes than the ones illustrated in FIGS. 4 to 8, as long as they are suitable to secure the implant (50) inside the cannula (30) and/or the cannula holder (22). Therefore, the arm (42) may be longer or shorter, thicker or thinner, and may adopt different shapes, such as, but not limited to, a cylinder, a prism, a protrusion or a bulk piece, as long as it can enter, in its first position, at least partially inside the lateral opening (34) of the cannula (30) to block the passageway.

It is further noted that the two positions of the arm (42) may present a positional tolerance, therefore the first and second position may not be exactly defined by an angular position or distance, and these positions may be defined as a function of the interaction of the arm (42) with the implant (50). Therefore, in its first position, see FIGS. 5 and 6, the arm (42) may at least be partially introduced within the lateral opening (34) of the cannula (30), and it may be more or less introduced inside the cannula (30) through the lateral opening (34), i.e. it may occupy a bigger or smaller cross section of the cannula (30) lumen, as long as it blocks the passageway of the implant (50) towards the exit or aperture (32) of the cannula (30). Similarly, the second position of the arm (42), see FIG. 7, may be defined as any position of the arm (42) that does not block the passageway of the implant (50) towards the exit or aperture (32) of the cannula (30) in its distal end. Therefore, in some embodiments, it may be still partially inside the lateral opening (34) of the cannula (30), or push the skin (52) of a patient at least partially inside the lateral opening (34) of the cannula (30), as long as it does not block the implant (50). Alternatively, the arm (42), in its second position, may be outside the lateral opening (34) of the cannula (30), more or less further away from said opening (34), and therefore not blocking the implant (50). Besides, the second position of the arm (42), as shown in FIG. 7, may also be defined as the position at which the arm (42) may rest after being lifted by the skin (52) of a patient, and therefore it may vary as a function of the thickness of the skin (52), the speed of insertion of the cannula (30) under the skin (52), or any other parameter that may alter its final position. Therefore, it may be considered the arm (42) is in its second position as long as it allows the implant to exit the cannula (30) through the aperture (32) on its distal end.

Advantageously, by allowing the skin (52) of a patient to set up the second position of the arm (42), until which moment the implant (50) was secured inside the cannula (30), the applicator (1) of the invention is able to secure the implant (50) until the very last moment of the application, avoiding unwanted displacements of the implant (50) until the cannula (30) is introduced under the skin (52). Furthermore, by securing the implant (50) inside the cannula (30) until its delivery, by blocking the passageway with the arm (42), any risk of damaging or fracturing said implant (50) before the skin (52) of the patient lifts the arm (42), i.e., when the implant is already being inserted, is thus avoided. This way it is guaranteed that an undamaged and unscathed implant (50) is introduced intradermally. The applicator (1) of the invention provides then an effective way of securing the implant at all times, until the exact moment in which it is needed to release the implant (50), once the cannula (30) is inserted. This avoids requiring additional elements to secure the implant (50) or to switch the arm (42) from the first to the second position, making the applicator (1) simple and enduring, and preventing the implant (50) from sliding out completely or partially, or moving inside the cannula (30), at any undesired moment.

In a preferred embodiment, the applicator (1) of the invention further comprises elastic means (70) that interacts with the mechanism (40) to push the arm (42) to the first position and into the lateral opening (34) of the cannula (30), preferably the elastic means (70) is a bended surface (70) or a spring, more preferably it is metallic.

Figure 8:
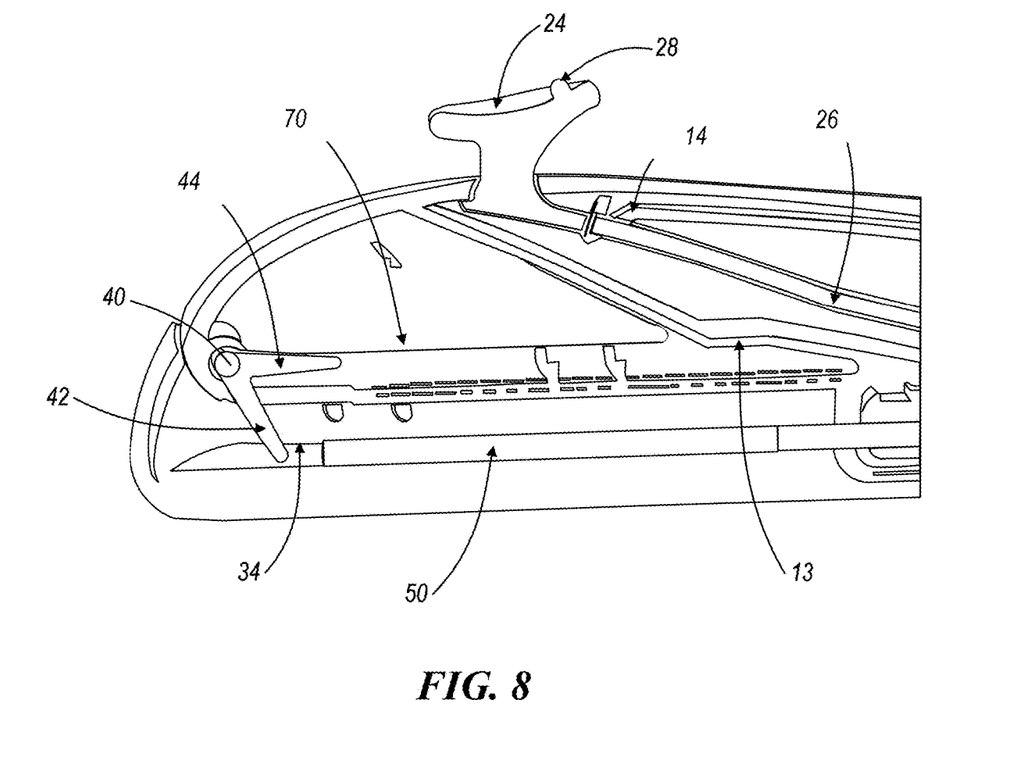
FIG. 8 shows a cross sectional side close-up view of the front part of an applicator according to one or more preferred embodiments of the invention.

The elastic means (70), see FIG. 8, may adopt various forms and configurations different than the ones illustrated in the figures, adapted to provide the necessary force to push the arm (42) into the first position. In a preferred embodiment, the elastic means (70) may be a bended surface, designed to exert a specific amount of mechanical pressure on the arm (42). In an alternate embodiment, the elastic means (70) may be a spring, which may be either a coil spring or a leaf spring. More preferably, the material of the elastic means (70) is metallic, such as stainless steel or a titanium alloy, to ensure durability and reliable performance, but it may also comprise other suitable materials, such as plastic or rubber. The elastic means (70) may also have varying dimensions, stiffness, and other mechanical properties to suit specific requirements of the applicator (1).

The mechanism (40) shown in FIGS. 4 to 8 comprises also a protrusion (44), similar to the arm (42), that is connected to said arm (42) and configured to interact with the elastic means (70). This interaction allows pushing the arm (42) to the first position, since they are connected. When the skin (52) of a patient displaces the arm (42) to its second position, outside of the lateral opening (34), the protrusion may compress the elastic means (70), as is shown in FIG. 7. The protrusion (44) and the arm (42) shown in FIGS. 4 to 8 have a similar shape and size, however, it is noted that in other embodiments they may be different, therefore the protrusion (44) may be longer or shorter, thicker or thinner, or adopt different shapes than the arm (42), as long as it allows the interaction with the elastic means (70). The mechanism (40) and/or the arm (42) illustrated in FIGS. 4 to 8 are rotatable, which allows the arm (42) to rotate between a first and a second position, however, in different embodiments the mechanism (40) and/or the arm (42) may not be rotatable, and instead they may be slidable, flexible, or any combination thereof, among other options that would allow the arm (42) to switch between the first and the second position. Alternatively, in different embodiments, the mechanism (40) may not comprise a protrusion (44), and instead the arm (42) or the mechanism (40) may interact directly with the elastic means (70). In some other embodiments, the elastic means (70) may be comprised in the mechanism (40), and/or the mechanism (40) may not comprise the arm (42), for instance by allowing the mechanism (40) or the elastic means (70) to enter at least partially trough the lateral opening (34), taking over the function of the arm (42).

It is further noted that the first and second positions of the arm (42) may be affected by the temperature, the wear and tear, the material, or the quality of the elastic means (70), or any other parameter that affect said elastic means (70), and therefore the skilled person would choose different elastic means (70) configurations to guarantee that the arm (1) can switch between the first and second position during operation of the applicator (1).

Advantageously, the inclusion of the elastic means (70) automates the securing process of the implant (50), by ensuring that the arm (42) is naturally biased towards the first position within the lateral opening (34). This makes the implantation process more reliable, minimizes the chance of operator error, and ensures consistent and reproducible placement of the implant (50), thereby improving the efficacy and safety of the implantation process.

In another preferred embodiment of the invention, the applicator (1) further comprises a stopper surface (19) that surrounds the cannula (30) and/or the cannula holder (22), and defines the limit of insertion of the cannula (30) under the skin (52) of a patient.

In FIG. 7 we can see an example of a stopper surface (19) that limits the insertion of the cannula (30) under the skin (52) of a patient. The stopper surface (19) displayed in FIG.

7 is rounded and surrounds the cannula holder (22). However, this illustration is not limiting, and said stopper surface (19) may adopt different shapes, or may not surround the cannula holder, or may be positioned relative to the cannula (30) in a different way. Similarly, the stopper surface (19) may be comprised inside the housing (10) of the applicator (1), or be an additional element that comprises different materials more suitable to set an stop in the inserting of the cannula (30) under the skin, such as rubber or any other material that feels more comfortable to the touch. It is noted that if there wasn't a stopper surface (19), the clinician or operator of the applicator (1) would need to decide until which point introduce the cannula (30), giving room to errors and unnecessary damage of the skin or the tissue below the skin.

According to a preferred embodiment of the invention, the applicator (1) further comprises a rod (82) mounted on or in the housing (10) and at least partially inside the cannula (30) and/or the cannula holder (22); and an actuator (24) for sliding the cannula (30) and the rod (82) relative to each other to expel the implant (50) from the cannula (30).

Figure 4:
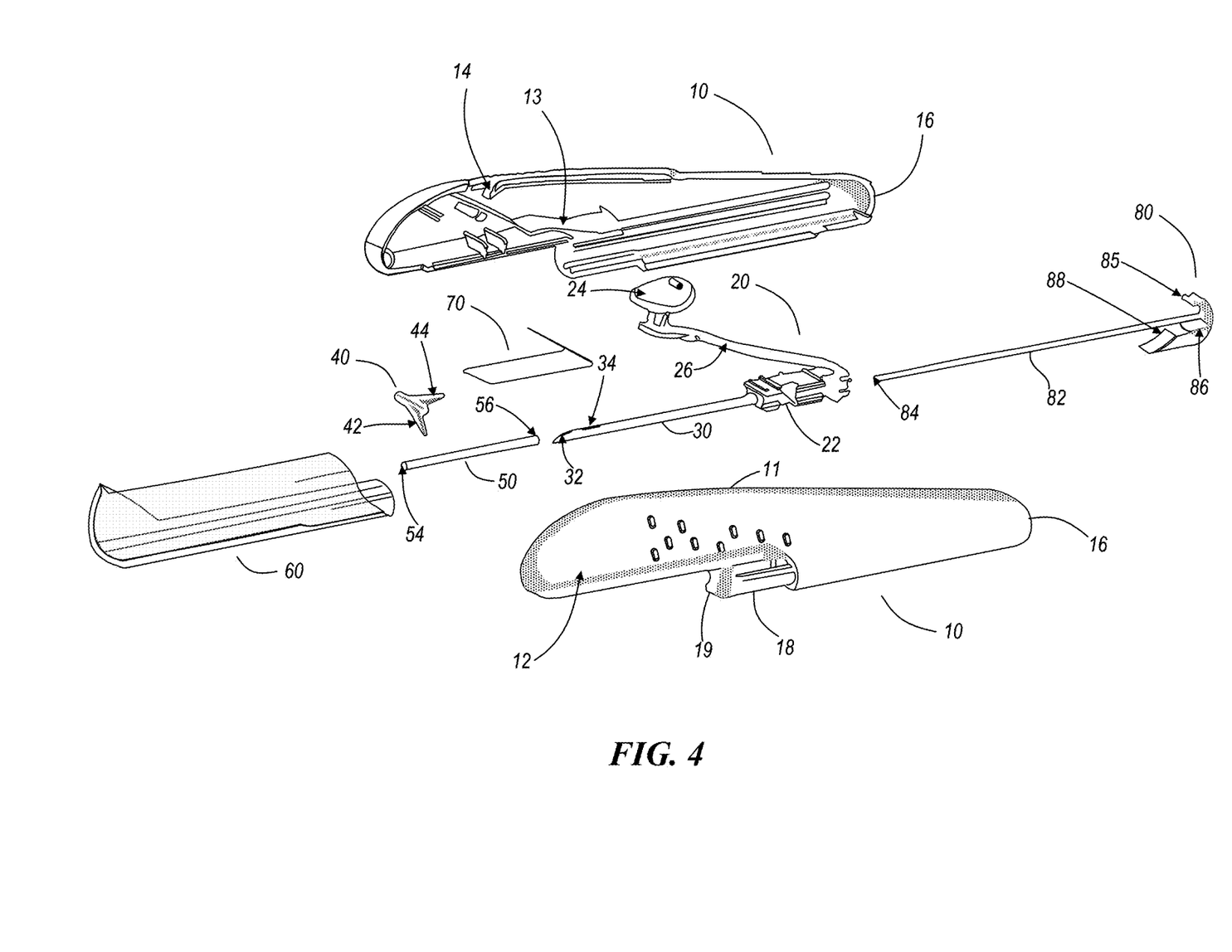
FIG. 4 shows an exploded view of an applicator according to one or more preferred embodiments of the invention.
Figure 5:
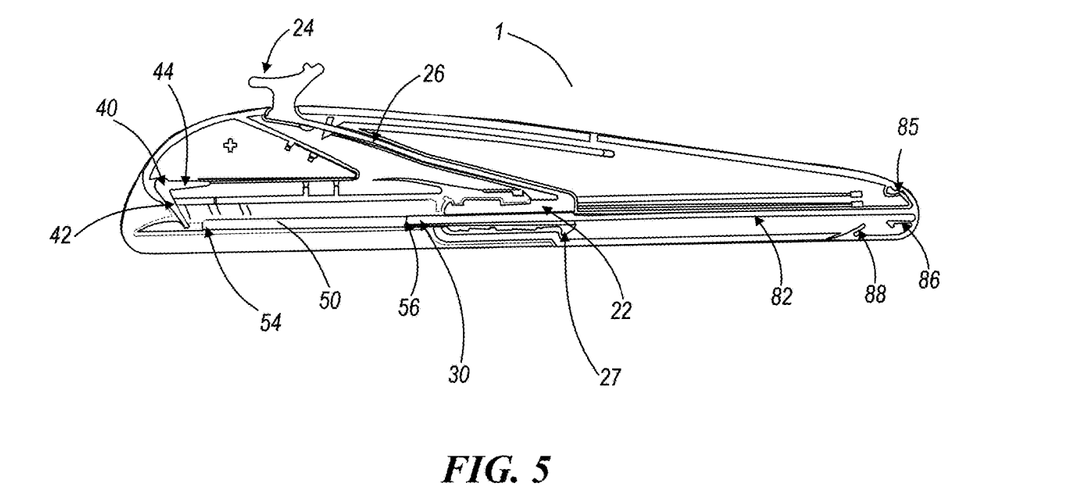
FIG. 5 shows a cross sectional side view of an applicator comprising a protective cover according to one or more preferred embodiments of the invention.

It is noted that the rod (82), may present different lengths and diameters than those illustrated in FIGS. 4 and 5, to accommodate different implant sizes or surgical needs, or comprise a squared or any other geometrical shape instead of a cylinder, as long as it allows to displace the implant (50) relative to the cannula (20) and/or the cannula holder (22). The rod (82) may comprise different materials, such as, but not limited to, metals, plastics, or composites.

The actuator (24), see FIGS. 1, 2 and 5, serves the purpose of sliding the cannula (30) and the rod (82) relative to each other, facilitating the expulsion of the implant (50) from the cannula (30). Although the accompanying figures may depict a specific shape for ease of manual operation, the actuator (24) can have various ergonomic designs. It may be adapted to interface comfortably with a user's finger, most preferably the thumb, and could be made rounded, squared, or in any other shape that allows effective operation. The material of the actuator (24) can also vary, from metals to plastics or rubber, depending on design needs and sterilization requirements.

In some embodiments, as is shown in FIGS. 5 to 7, the distal end (84) of the rod (82) is inside the proximal end of the cannula holder (22) and the proximal end of the cannula (30). According to some embodiments, the implant (50) may be positioned between the lateral opening (34) of the cannula (30), and the distal end (84) of the rod (82), preferably the proximal end (56) of the implant (50) is adjacent to the distal end (84) of the rod (82). However, it is noted that in some other embodiments the distal end (84) of the rod (82) may not be inside the proximal end of the cannula (30) and/or the cannula holder (22), such as, for example, if the distal end (84) of the rod (82) is initially outside the cannula (30) and/or the cannula holder (22) and it moves towards the distal end of the cannula (30) at the same time that the cannula (30) moves towards the proximal end of the rod (82) upon application, in a combined movement. Therefore, the skilled person may find alternative initial positions and relative displacements of the rod (82), the cannula (30) and/or the cannula holder (22) as long as the applicator (1) allows to insert the implant (50) under the skin of a patient (52).

Advantageously, the rod (82), in combination with the actuator (24), provides an additional layer of control and stability during the implant insertion process, facilitating an easy and smooth operation, thereby reducing the potential for user error and improving the overall reliability of the implant placement.

In a more preferred embodiment of the applicator (1) of the invention, the housing (10) further comprises a handle (12) for grasping and maneuvering the applicator (1) and the cannula (30) during insertion of an implant (50), preferably wherein the actuator (24) is located on the handle (12).

It is noted that the handle (12) serves as a means for grasping and maneuvering the applicator (1) during the implant (50) insertion process. While the FIGS. 1 to 7 may illustrate one possible design of the handle (12), it may take different forms to suit different hand sizes or gripping styles. For example, the handle (12) may be straight, curved, or contoured. Additionally, it may feature grooves, raised sections, or rubberized coatings to facilitate gripping. In a more preferred embodiment of the invention, the handle (12) and/or the actuator (24) are provided with surface parts that have a relatively high coefficient of friction, wherein preferably they comprise at least one or more protrusions (11, 28) to improve the grip over the surface. It is further noted that the handle (12) may comprise different materials that range from plastics to metals, and may also include composite materials or rubber coatings. Some examples are, but it is not limited to, polyethylene terephthalate, polypropylene, high-density polyethylene, polyvinyl chloride, stainless steel, aluminium, silicone rubber, and carbon-fibre composites. These materials may be selected to provide not only durability but also comfort and increased friction for secure grasping. It is also noted that any other part of the applicator (1) may comprise any of these materials, such as the housing (10), the actuator (24) or any of the different elements.

It is further noted that the actuator (24) is preferably located on the handle (12). This configuration allows for more intuitive and one-handed operation of the applicator (1). The actuator (24) may be positioned in various locations on the handle (12) for optimum ease of use, such as on the top, side, or bottom of the handle (12). The shape of the actuator (24) can also be tailored for easy actuation, including but not limited to rounded, square, oblong, or custom shapes designed to fit a human finger, most preferably the thumb. Various materials could be used for the actuator (24), including the ones above mentioned.

Advantageously, having a handle (12), preferably with the actuator (24) integrated therein, enables one-handed operation, thus freeing the other hand of the user for other tasks or for stabilizing the implantation area. This significantly enhances the user's ability to precisely control the implant (50) insertion process. Furthermore, the ergonomic designs and material choices for the handle (12), such as the design illustrated in FIGS. 1 to 7, may add comfort and reduce user fatigue, thereby making the implant (50) insertion process more efficient and reliable.

In another more preferred embodiment of the applicator (1), the cannula holder (22) is slidable over the rod (82), and wherein the actuator (24) and the holder (22) are interconnected, preferably by a flexible element (26), more preferably wherein the flexible element (26) is at least partially retained by guides (13).

Figure 9:
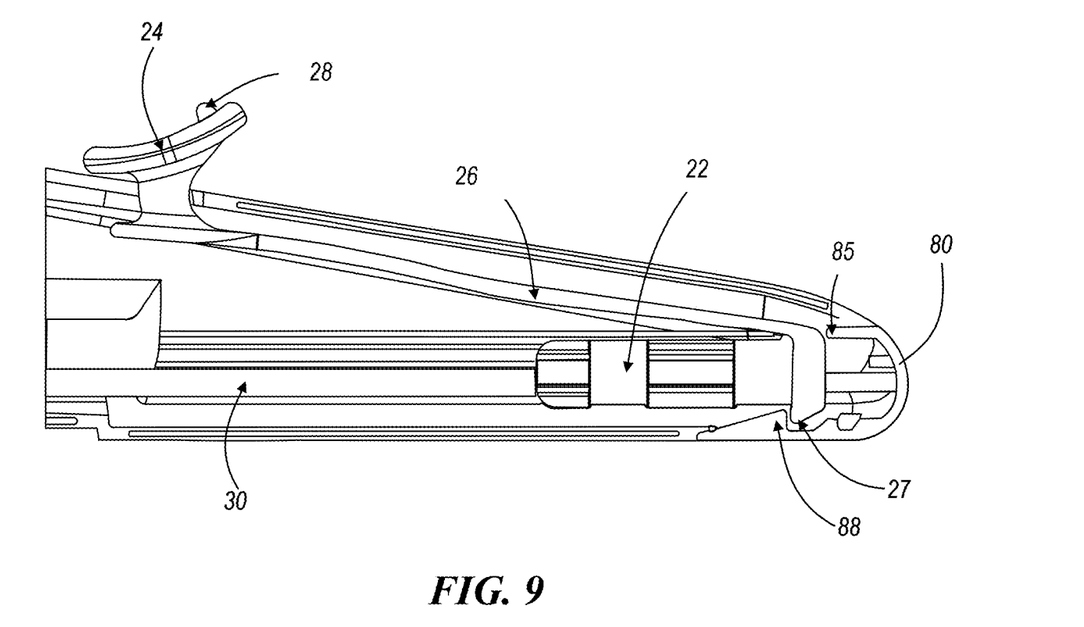
FIG. 9 shows a cross sectional side close-up view of the rear part of an applicator with the actuator in a final position, according to one or more preferred embodiments of the invention.

It is noted that the sliding relationship between the cannula holder (22) and the rod (82) allows for an adjustable positioning of the implant (50) relative to the cannula (30), providing versatility for different implantation depths or types of procedures. While the embodiment examples illustrated in FIGS. 7 and 9 show that the rod (82) slides inside the cannula holder (22) through an aperture in the cannula holder (22) in the shape of the rod (82), i.e. cylindrical, and at least the size of the rod (82), preferably a bit bigger, such as a 50, 25, 15, 10 or 5 percent bigger in diameter, in different embodiments it may be realized through various types of rails, grooves, or interlocking features. The materials for these sliding mechanisms could include, but are not limited to, polyethylene terephthalate, polypropylene, high-density polyethylene, polyvinyl chloride, stainless steel, aluminium, silicone rubber, and carbon-fibre composites.

It is noted that the cannula holder (22) is slidable over the rod (82). This sliding relationship allows for adjustable positioning of the cannula (30) relative to the housing (10), providing versatility for different implantation depths or types of procedures. While the exemplary embodiment may show a specific kind of sliding mechanism, it could be realized through various types of rails, grooves, or interlocking features. The materials for these sliding mechanisms could include, but are not limited to, polyethylene terephthalate, polypropylene, high-density polyethylene, polyvinyl chloride, stainless steel, aluminium, silicone rubber, and carbon-fibre composites.

It is further noted that the interconnection between the actuator (24) and the cannula holder (22) may be achieved by various means, but preferably through a flexible element (26). This element could take various forms including, but not limited to, a flexible flange, a wire or a cord. The material of the flexible element (26) may also vary widely and may include materials such as, but not limited to, any of the above mentioned. More preferably, the flexible element (26) is at least partially retained by guides (13), which may consist of channels, loops, or any other guiding structures, preferably comprised in the housing (10).

It is also noted that in FIGS. 5 to 7, it is illustrated a cross section lateral view of the applicator (1), therefore the implant (50), even though it is inside the cannula (30), is visible.

Advantageously, the sliding relationship between the cannula holder (22) and the rod (82), as well as the interconnection between the actuator (24) and the holder (22), add a layer of adaptability and control to the applicator (1). The interconnection between the actuator (24) and the cannula holder (22) ensures synchronized operation, reducing the chance of misalignment or error during the implantation process.

In another more preferred embodiment of the applicator (1) of the invention, the housing (10) further comprises a protrusion (14) that blocks the actuator (24) in an initial position before actuating the applicator (1) and prevents it from sliding towards the proximal end (16) of the housing (10), preferably until it is pushed to evade said protrusion (14), more preferably until it is pushed downwards to evade said protrusion (14).

In FIGS. 4 and 8 it is illustrated an embodiment of an actuator (1) comprising a protrusion (14) that blocks the actuator (24) in an initial position. While the figures may depict a particular type of protrusion (14), it should be understood that this feature may present various forms and materials. For example, the protrusion (14) may be a ridge, a nub, a tab, or even a spring-loaded pin. It may comprise materials that are rigid or semi-rigid, such as metals like stainless steel or aluminium, plastics like polycarbonate or ABS, ceramic materials, or any other material above mentioned for other parts of the applicator (1). Furthermore, the protrusion (14) may be overcome by pushing it downwards, however alternative mechanisms for overcoming the protrusion could include twisting, squeezing, or a combination thereof.

Advantageously, the incorporation of the protrusion (14) into the housing (10) serves as a safety feature by preventing unintentional actuation of the applicator (1), thereby reducing the risk of premature implant (50) deployment or user error. Also, it provides tactile feedback to the user, signaling that the actuator (24) is securely positioned in its initial state and ready for intentional actuation.

In a preferred embodiment of the invention, the applicator (1) further comprises a back cover (80) attached to the rod (82), preferably wherein the back cover (80) is not removable from the proximal end (16) of the housing (10).

The back cover (80) may preferably not be removable from the proximal end (16) of the housing (10). This allows to introduce the implant (50) inside the cannula (30) from the back or proximal end of the applicator (1), before finishing the assembly of said applicator (1). Once the implant is placed in position inside the cannula (30), the back cover (80) may be easily placed to block the implant from sliding out through the back of the applicator (1). By not being removable, it is guaranteed that the back cover (80) will not be unwantedly removed, and the implant (50) thus will not be allowed to exit through the proximal end of the cannula (30) or the proximal end of the applicator (1). It is noted that after the placement of the implant (50) inside the cannula (30), the rod (82) may be configured to push said implant (50) through the cannula (30) towards the aperture (32). While in FIG. 9 it is illustrated one type of back cover (80) with hooks and protrusions that allow an easy insertion, but prevent its removal, various alternatives could be employed. For instance, the back cover (80) could be hinged, threaded, or snap-fit onto the housing (10). The material for the back cover (80) could include a wide range of options such as the ones already mentioned for any other element of the applicator (1). It is further noted that in some other embodiments the back cover (80) could be removable, allowing the implant (50) to be loaded from the rear or the proximal end of the cannula (30) by removing the back cover (80), after an initial assembly of the applicator (1).

It is noted that the implant (50) may also be loaded from the distal end of the cannula (30) once the back cover (80) is assembled, by manually or by use of external means to move the arm (42) to its second position during loading of the implant (50) to allow the passageway to the inside of the cannula (30).

Advantageously, the inclusion of the back cover (80) facilitates the loading of the implant (50) into the cannula (30) before the final assembly, while preventing it to be removed after the implant (50) is loaded and the back cover (80) is placed in the applicator (1).

In a more preferred embodiment of the applicator (1), the back cover (80) further comprises a flange (88) that engages with a protrusion (27) in the cannula holder (22), which blocks the actuator (24) in a final position after actuating the applicator (1).

FIG. 9 shows an example of a flange (88) engaged with the protrusion (27) of the cannula holder (22) according to one or more embodiments of the invention. It is noted, however, that various configurations could be utilized. For example, the flange (88) could have a variety of shapes, including but not limited to a spike, a dent, circular, rectangular, or even irregular shapes to effectively engage with the corresponding protrusion (27) of the cannula holder (22). The protrusion (27) itself could be a dent, a spike, a rectangular shape, a raised lip, a notch, or even a threaded section that securely interacts with the flange (88). The materials for the flange (88) and protrusion (27) could include any material afore mentioned for any other part of the applicator (1).

Advantageously, the inclusion of the flange (88) and the protrusion (27) provides additional operational benefits to the applicator (1). Specifically, their interaction ensures that the actuator (24) is securely locked in a final position after the applicator (1) has been actuated, thereby preventing unintended or accidental reverse movements. This locking feature enhances the reliability of the implant (50) placement process, adding an extra layer of safety and assurance for both the healthcare provider and the patient.

In a preferred embodiment of the applicator (1) of the invention, the implant (50) comprises an active substance for insertion under the skin of a patient, preferably the implant (50) contains a progestogenic hormone, more preferably contains etonogestrel.

It is noted that various active substances may be utilized. Examples of such active substances could range from hormones, antibiotics, antiseptics, analgesics to anti-inflammatory agents. Preferably hormones are used, and they could be of various types such as estrogenic, androgenic, or even a combination thereof. More preferably the active substance is a progestogenic hormone such as etonogestrel, or other progestogenic hormones that may comprise levonorgestrel, medroxyprogesterone acetate, or norethisterone, among others. Furthermore, the active substance could be contained in a core within the implant (50), coated onto the implant (50), or even impregnated throughout the implant (50) material.

Advantageously, the ability to incorporate a variety of active substances, including progestogenic hormones like etonogestrel, broadens the applicability and usefulness of the applicator (1). It enables targeted and localized drug delivery, offering a highly efficient method for the administration of various treatments. This is particularly beneficial in providing a sustained release of medication over an extended period, thereby potentially improving patient compliance and treatment outcomes. Moreover, the versatility in the form and type of active substance allows for customization based on specific medical requirements, thereby maximizing therapeutic efficacy.

According to a preferred embodiment of the invention, the applicator (1) is configured to allow the insertion of an implant (50) inside the cannula (30) and/or cannula holder (22) through the proximal end (16) of the housing (10) before assembling the back cover (80). Alternatively, the back cover (80) may be removable, and the applicator (1) may be configured to allow the insertion of an implant (50) inside the cannula (30) and/or cannula holder (22) through the proximal end (16) of the housing (10) after removing the back cover (80).

It is noted that in different embodiments, the implant may be loaded into the cannula (30) and/or cannula holder (22) from the distal end, through the aperture (32) on the distal end of the cannula (30) once the back cover (80) is assembled, by manually or by use of external means to move the arm (42) to its second position during loading of the implant (50) to allow the passageway to the inside of the cannula (30). Alternatively, a side loading feature could be introduced to allow the implant (50) to be inserted through a side port in the cannula (30) or cannula holder (22). The design may also include interacting with locking mechanisms (40) to secure the implant (50) in place within the cannula (30) or cannula holder (22) after it has been inserted.

Advantageously, the ability to load the implant (50) into the cannula (30) and/or cannula holder (22) from the proximal end (16) of the housing offers increased versatility in how the applicator (1) may be used and loaded. This feature simplifies the loading process, making it more convenient and potentially faster. Additionally, the option to insert the implant (50) from various directions increases the device's adaptability for different implant types and sizes, enhancing the overall utility and efficiency of the applicator (1).

According to another preferred embodiment of the invention, the applicator (1) further comprising a protective cover (60) for the cannula (30) and/or the cannula holder (22). In FIGS. 2, 5 and 8 we can observe an example of semi-transparent protective cover (60) according to one or more embodiments of the invention.

It is noted that the protective cover (60) may be made from opaque, transparent, or translucent materials. The materials for the protective cover (60) may include, but are not limited to, polyethylene terephthalate, polypropylene, high-density polyethylene, polyvinyl chloride, stainless steel, aluminium, silicone rubber, and carbon-fibre composites. Additionally, the protective cover (60) may be implemented in different shapes, including but not limited to, rectangular, cylindrical, conical, or a combination thereof, or with the edges more or less softened. The protective cover (60) may also feature locking mechanisms to secure it in place, such as snap-fit locks, threads, or magnetic couplings. Furthermore, the protective cover (60) may have additional features, such as vents, perforations, or even antimicrobial coatings to promote sterility.

Advantageously, the inclusion of the protective cover (60) enhances the safety and sterility of the applicator (1) by shielding the cannula (30) and/or cannula holder (22) from potential contaminants. This is particularly beneficial in medical settings to reduce the risk of infection.

In a more preferred embodiment of the applicator (1) of the invention, the arm (42) is configured to remain in the same position independently of the removal or the application of the protective cover (60) the cannula (30) and/or the cannula holder (22).

It is noted that the arm (42) may be designed to remain in a consistent position regardless of whether the protective cover (60) covering the cannula (30) is applied or removed. Preferably, the arm (42) remains in its first position regardless of the removal or application of the protective cover (60). As it can be seen in FIGS. 5 and 6 that illustrate one or more embodiments of the applicator (1) with and without the protective cover (60), the arm (42) retains its initial position in both configurations.

Advantageously, not having any dependence in the position of the arm (42) with respect to the presence or not of the protective cover (60), particularly when the arm is in its first positions, allows to continuously secure the implant (50) inside the cannula (30), even when the protective cover (60) is removed prior to the insertion of the cannula (30) under the skin (52) of a patient.

According to a preferred embodiment of the invention, the applicator (1) further comprises a safety element (250) configured to prevent the actuator (24) from being pushed to evade the protrusion (14). Therefore, the actuator (24) cannot be actuated even if pushed, further preventing an unintentional actuation.

The safety element (250) advantageously, prevent the actuation of the actuator (24) in uncontrolled environments, such as transport, which could lead to an unintentional actuation due to movement. Such an scenario would imply that the cannula (30) and the rod (82) would lead relative to each other leading to scenarios ranging from damaging the implant (50) to making the applicator (1) unusable. This further enables the transport of the applicator (1) without the need for a hard case or protective element that prevents the involuntary actuation of the actuator (24) further reducing space, weight and costs of transport and storing of the applicators.

It is noted that safety element (250) can take different shapes and forms, such as pin-locks, ratchet mechanism or safety pins among others. The skilled person may envisage many ways in which the applicator (1) may comprise a safety element (250) configured to prevent the actuator (24) from being pushed to evade the protrusion (14).

Figure 10A:
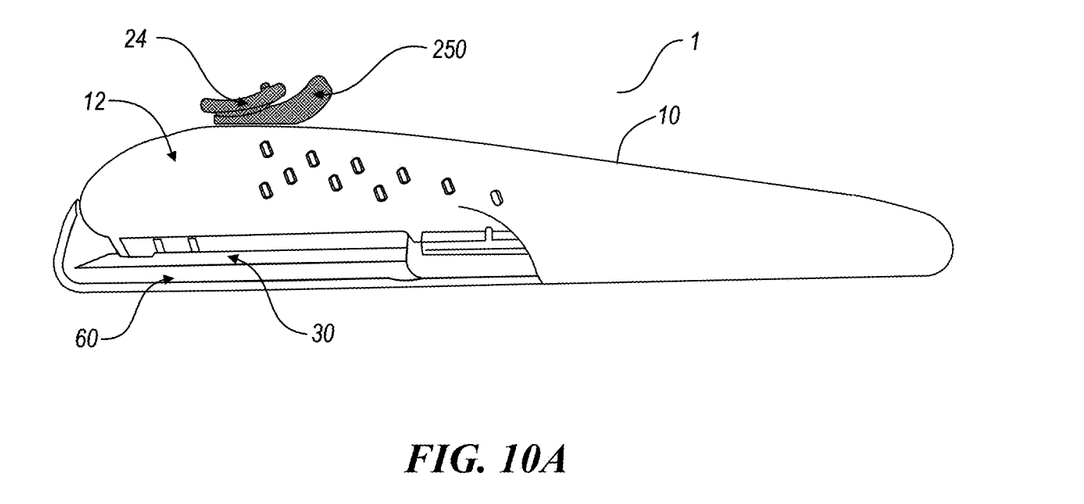
FIG. 10A shows a lateral view of an applicator comprising a safety device according to one or more preferred embodiments of the invention.
Figure 10B:
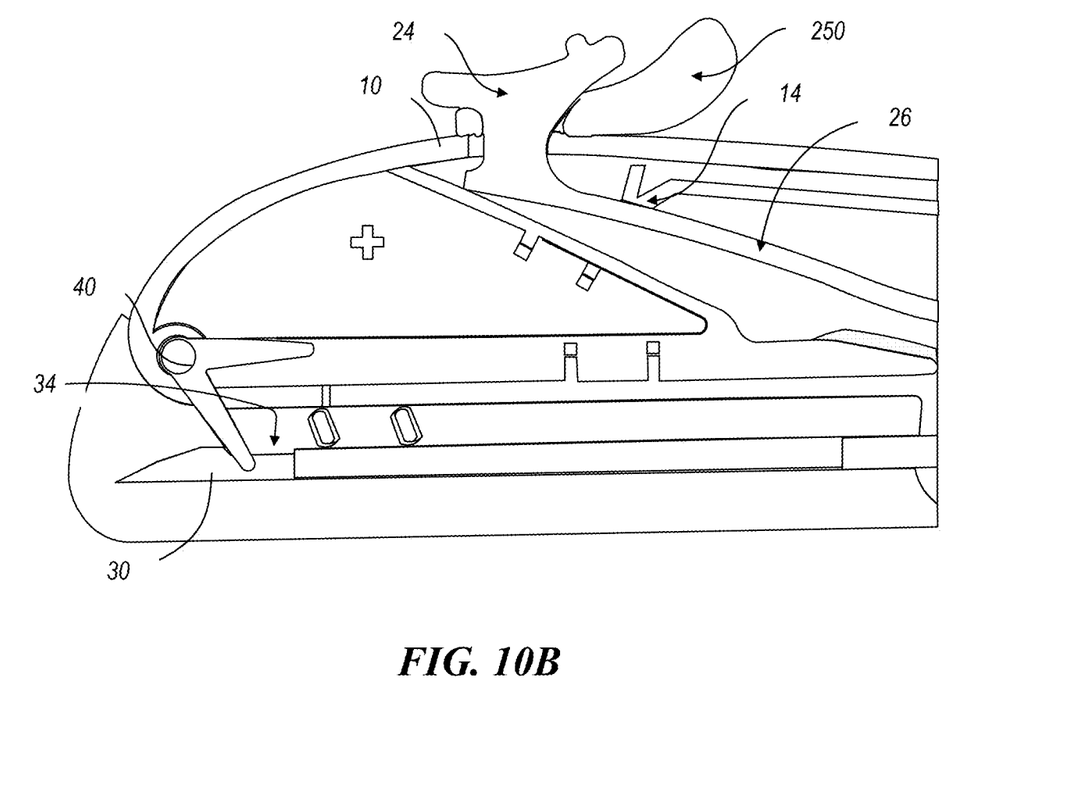
FIG. 10B shows a cross sectional side close-up view of the applicator of FIG. 10A, according to one or more preferred embodiments of the invention.

In a particular preferred embodiment and as shown with respect to FIGS. 10A and 10B, the safety element (250) is configured to be placed between the actuator (24) and the housing (10), such that the actuator (24) cannot be pushed relative to the housing (10). In a more preferred embodiment, the safety element (250) has the form of a safety pin and comprises an open ring shape and is configured to be sided around the actuator (24). In this embodiment, the safety pin (250) prevents the actuator (24) from being pushed to evade the protrusion (14), by blocking the actuator movement towards the housing (10). Advantageously the safety element (250) can be easily pulled out when the applicator is to be used.

All of the above are fully within the scope of the present disclosure, and are considered to form the basis for alternative embodiments in which one or more combinations of the above described features are applied, without limitation to the specific combination disclosed above.

In light of this, there will be many alternatives which implement the teaching of the present disclosure. It is expected that one skilled in the art will be able to modify and adapt the above disclosure to suit its own circumstances and requirements within the scope of the present disclosure, while retaining some or all technical effects of the same, either disclosed or derivable from the above, in light of his common general knowledge in this art. All such equivalents, modifications or adaptations fall within the scope of the present disclosure.

The invention claimed is:

1. An applicator for inserting an implant under the skin of a patient, comprising:
   a) a housing;
   b) a cannula, fixed to a cannula holder, which is slidably received inside the housing, wherein the cannula comprises a lumen, an aperture on its distal end and a lateral opening;
   c) an implants having a surface facing the distal end of the cannula accommodated inside the cannula and/or the cannula holder, and
   d) a mechanism that secures the implant inside the cannula—and/or the cannula holder, wherein the mechanism comprises an arm which is rotatable and/or slidable and/or flexible between a first position, wherein the arm prevents the implant from exiting the cannula through the aperture, and a second position, wherein the arm allows the implant to exit the cannula through the aperture, thereby allowing placement of the implant under the skin of the patient;
   wherein:
   e) the lateral opening of the cannula is positioned between the aperture of the cannula and the distal facing surface of the implant, and;
   f) in the first position, the arm is configured to engage the distal facing surface of the implant and—secure the implant inside the cannula by blocking passage of the implant through the cannula lumen toward the aperture.

2. The applicator according to claim 1, wherein said applicator is configured such that when the cannula is inserted under the skin of a patient, skin on top of the cannula sets the arm into its second position, outside of the lateral opening of the cannula, such that it allows the implant to slidably exit the cannula through the aperture.

3. The applicator according to claim 1, further comprising an elastic piece that interacts with the mechanism to push the arm to the first position and into the lateral opening of the cannula.

4. The applicator according to claim 3, wherein the elastic piece is a bent surface or a spring.

5. The applicator according to claim 4, wherein the elastic piece is metallic.

6. The applicator according to claim 1, further comprising a stopper surface that surrounds the cannula and/or the cannula holder, and defines the limit of insertion of the cannula under the skin of a patient.

7. The applicator according to claim 1, further comprising a rod mounted on or in the housing and at least partially inside the cannula and/or the cannula holder; and an actuator for sliding the cannula and the rod relative to each other to expel the implant from the cannula.

8. The applicator according to claim 7, wherein the housing further comprises a handle for grasping and maneuvering the applicator and the cannula during insertion of the implant.

9. The applicator according to claim 8, wherein the handle and/or the actuator are provided with surface parts that have a coefficient of friction higher than the rest of the handle and/or actuator.

10. The applicator according to claim 9, wherein the surface parts comprise at least one or more protrusions to improve the grip over the surface.

11. The applicator according to claim 8, wherein the actuator is located on the handle.

12. The applicator according to claim 7, wherein the cannula holder is slidable over the rod, and wherein the actuator and the cannula holder are interconnected.

13. The applicator according to claim 12, wherein the actuator and the cannula holder are interconnected by a flexible element.

14. The applicator according to claim 13, wherein the flexible element is at least partially retained by guides.

15. The applicator according to claim 7, wherein the housing further comprises a protrusion that blocks the actuator in an initial position before actuating the applicator and prevents it from sliding towards the proximal end of the housing.

16. The applicator according to claim 15, wherein the protrusion blocks the actuator in the initial position before actuating the applicator and prevents it from sliding towards the proximal end of the housing until it is pushed to evade said protrusion.

17. The applicator according to claim 1, further comprising a back cover attached to the rod.

18. The applicator according to claim 17, wherein the back cover further comprises a flange that engages with a protrusion in the cannula holder, which blocks the actuator in a final position after actuating the applicator.

19. The applicator according to claim 17, wherein the back cover is not removable from the proximal end of the housing.

20. The applicator according to claim 1, wherein the implant comprises an active substance for insertion under the skin of a patient.

21. The applicator according to claim 20, wherein the implant comprises a progestogenic hormone.

22. The applicator according to claim 20, wherein the implant comprises etonogestrel.

23. The applicator according to claim 1, wherein said applicator is configured to allow the insertion of the implant inside the cannula and/or cannula holder through the proximal end of the housing before assembling the back cover.

24. The applicator according to claim 1, further comprising a protective cover for the cannula and/or the cannula holder.

25. The applicator according to claim 24, wherein the arm is configured to remain in the same position independently of the removal or the application of the protective cover, the cannula, and/or the cannula holder.

* * * * *

UNITED STATES PATENT AND TRADEMARK OFFICE
CERTIFICATE OF CORRECTION

PATENT NO. : 12,377,253 B2
APPLICATION NO. : 18/488828
DATED : August 5, 2025
INVENTOR(S) : Alessandro Castellucci et al.

Page 1 of 1

It is certified that error appears in the above-identified patent and that said Letters Patent is hereby corrected as shown below:

In the Claims

Column 17, Claim 1, Line 47:
"an implants having" should read: --an implant having--.

Signed and Sealed this
Sixth Day of January, 2026

John A. Squires
*Director of the United States Patent and Trademark Office*